United States Patent
Nishino et al.

(10) Patent No.: US 9,920,293 B2
(45) Date of Patent: Mar. 20, 2018

(54) SACCHARIFICATION REACTION APPARATUS

(71) Applicant: KAWASAKI JUKOGYO KABUSHIKI KAISHA, Kobe-shi, Hyogo (JP)

(72) Inventors: Takashi Nishino, Suita (JP); Noriaki Izumi, Kobe (JP); Hironori Tajiri, Kobe (JP); Hiromasa Kusuda, Kobe (JP); Masaki Tsuzawa, Kobe (JP)

(73) Assignee: KAWASAKI JUKOGYO KABUSHIKI KAISHA, Kobe-shi (JP)

( * ) Notice: Subject to any disclaimer, the term of this patent is extended or adjusted under 35 U.S.C. 154(b) by 304 days.

(21) Appl. No.: 14/758,341

(22) PCT Filed: Nov. 21, 2013

(86) PCT No.: PCT/JP2013/006843
§ 371 (c)(1),
(2) Date: Jun. 29, 2015

(87) PCT Pub. No.: WO2014/103148
PCT Pub. Date: Jul. 3, 2014

(65) Prior Publication Data
US 2016/0108355 A1    Apr. 21, 2016

(30) Foreign Application Priority Data
Dec. 27, 2012 (JP) .................................. 2012-284978

(51) Int. Cl.
C12M 1/00 (2006.01)
C12M 1/12 (2006.01)
(Continued)

(52) U.S. Cl.
CPC ............ *C12M 45/20* (2013.01); *C12M 29/00* (2013.01); *C12M 33/12* (2013.01); *C12M 37/04* (2013.01);
(Continued)

(58) Field of Classification Search
CPC ...... C12M 45/20; C12M 45/02; C12M 37/04; C12M 33/12; C12M 29/00; C13K 1/02; Y02E 50/16
See application file for complete search history.

(56) References Cited

U.S. PATENT DOCUMENTS

| 4,557,403 A | 12/1985 | Stevenson |
|---|---|---|
| 7,819,976 B2 * | 10/2010 | Friend ...................... C13K 1/02 127/1 |
| 2009/0053800 A1 | 2/2009 | Friend et al. |

FOREIGN PATENT DOCUMENTS

| JP | S62-102826 A | 5/1987 |
|---|---|---|
| JP | 2005-145697 A | 6/2005 |

(Continued)

OTHER PUBLICATIONS

Feb. 18, 2014 Search Report issued in International Patent Application No. PCT/JP2013/006843.
(Continued)

*Primary Examiner* — David A Reifsnyder
(74) *Attorney, Agent, or Firm* — Oliff PLC

(57) ABSTRACT

A saccharification-reaction apparatus includes: a reactor which causes a saccharification-reaction of a raw material; and a raw material charging device which charges the raw material into the reactor at a predetermined interval; the reactor includes: a heating steam feeder which increases a temperature of the raw material charged from the charging device to a saccharification-reaction temperature; and a feeding mechanism which sequentially feeds each of the charged raw materials toward an outlet-port in a predeter-
(Continued)

mined short period of time while causing the saccharification-reaction of each raw material under a high temperature and pressure; the raw material charging-device charges into the reactor, the raw material with a suitable bulk density for a saccharification-reaction speed of the reactor; in this manner, the saccharification-reaction apparatus charges the raw material in a hydrolytic saccharification state into the reactor by the raw material charging device; and hydrolytically saccharifying the raw material efficiently in the reactor.

7 Claims, 6 Drawing Sheets

(51) Int. Cl.
  *C12M 1/26* (2006.01)
  *C12M 1/33* (2006.01)
  *C13K 1/02* (2006.01)

(52) U.S. Cl.
  CPC ............... *C12M 45/02* (2013.01); *C13K 1/02* (2013.01); *Y02E 50/16* (2013.01)

(56) References Cited

FOREIGN PATENT DOCUMENTS

| | | |
|---|---|---|
| JP | 2006-007108 A | 1/2006 |
| JP | 2010/536558 A | 12/2010 |
| WO | 2009/096060 A1 | 8/2009 |
| WO | 2010/038302 A1 | 4/2010 |

OTHER PUBLICATIONS

Jun. 3, 2015 Office Action issued in Chinese Patent Application No. 201310635393.9.

\* cited by examiner

SACCHARIFICATION REACTION APPARATUS

TECHNICAL FIELD

The present invention relates to a saccharification reaction apparatus for charging, for example, a biomass raw material into a reactor by a raw material charging device and hydrolytically saccharifying the biomass raw material in the reactor.

BACKGROUND ART

As part of biomass energy utilization, attempts have been made to hydrolytically saccharify cellulose or hemicellulose, which are major components of plants such as bagasse and rice straw, and then obtain ethanol from its sugar solution. Ethanol thus obtained is planned to be utilized as part of a fuel by being mixed into an automobile fuel or utilized as an alternative fuel for gasoline.

One of the methods for decomposing cellulosic biomass containing cellulose or hemicellulose into saccharides is a method of hydrolytically saccharifying the cellulosic biomass by utilizing high-temperature and high-pressure supercritical or subcritical water.

One example of the method is as follows: charge a biomass raw material that is a ground product of bagasse, rice straw, or the like (such a biomass raw material may be simply referred to as a "raw material" in the description and claims herein) into a reactor; hydrolytically saccharify the raw material in the reactor to obtain a C5 sugar solution; and then further hydrolytically saccharify a dehydrated cake of the C5 sugar solution in a reactor to obtain a C6 sugar solution. Thereafter, these sugar solutions are fermented and distilled, and thereby ethanol is produced.

However, in the case of using such high-temperature and high-pressure supercritical or subcritical water, the hydrolytic saccharification of cellulose or hemicellulose is completed within a short period of time of several seconds to several minutes since the supercritical or subcritical water has strong oxidizing power.

Therefore, there is a strong demand for a saccharification reaction apparatus that is capable of increasing a saccharification rate by charging a biomass raw material in a suitable condition for such a short-time saccharification reaction into a reactor and hydrolytically saccharifying the biomass raw material efficiently in the reactor.

As a device for feeding this kind of biomass raw material and the like, there is a conventional feeding device configured to feed a to-be-treated object into a pressurized container. This device is configured such that the to-be-treated object in a hollow body provided with drainage means is pushed out of the hollow body by a piston through an opening facing the pressurized container (see Patent Literature 1, for example).

As another conventional art example, there is an injection device configured to feed a to-be-injected object containing slurry and solids into a high-temperature and high-pressure reactor by means of a piston moving inside a cylinder. For the purpose of preventing clogging due to the solids, this device is provided with a spindle extending through a through-hole of the piston (see Patent Literature 2, for example).

As yet another conventional art example, there is a dry feeder configured to cause finely divided solids to fall from a slot of a cylinder by gravity into a load chamber. After causing the solids to fall, the feeder closes the slot of the cylinder, and feeds the solids from the load chamber into a high-pressure reaction container by means of a piston (see Patent Literature 3, for example).

CITATION LIST

Patent Literature

PTL 1: Japanese Laid-Open Patent Application Publication No. 2005-145697
PTL 2: Japanese Laid-Open Patent Application Publication No. 2006-7108
PTL 3: Japanese Laid-Open Patent Application Publication No. S62-102826

SUMMARY OF INVENTION

Technical Problem

There is a method of charging a biomass raw material into a reactor, in which method, when the raw material is charged into the reactor, the raw material contains moisture and is in a state of being consolidated. However, if the raw material in such a consolidated state is charged into the reactor, it takes time to increase the temperature of the raw material to a saccharification reaction temperature. The reason for this is considered as follows: if the raw material in a consolidated state is charged into the reactor, the raw material tends to remain a mass and does not easily break into pieces; accordingly, the raw material cannot be quickly mixed with steam; and consequently the rate of temperature increase is low. For this reason, if the raw material in a consolidated state is charged into the reactor, the saccharification rate is reduced. The same is true in the case of feeding the raw material by the device disclosed in Patent Literature 1. Also in the case of the device disclosed in Patent Literature 2, it is difficult to quickly increase the temperature of the solids to a saccharification reaction temperature.

There is also a method of charging a raw material into a high-pressure reactor, in which method the raw material to be charged into the reactor is not consolidated. One example of the method is a charging method utilizing a general lock hopper. However, the charging method utilizing a lock hopper is as follows: open an upper gate valve and charge the raw material into the hopper in a low-pressure state, and close the upper gate valve; open a lower pressure-adjusting valve to adjust the pressure in the hopper to be a high pressure that is the same pressure as the pressure in the reactor, and then close the lower pressure-adjusting valve; subsequently, open a lower gate valve to charge the raw material into the reactor; then close the lower gate valve and open an upper pressure-adjusting valve to adjust the pressure in the hopper to be a low pressure, followed by closing of the upper pressure-adjusting valve; and thereafter, open the upper gate valve and charge the next raw material into the hopper. Therefore, in the case of performing the charging of the raw material by utilizing the lock hopper, charging intervals need to be set for allowing these steps to be repeated in the charging intervals. These steps are performed, for example, once in every two to three minutes, i.e., at charging intervals of two to three minutes.

However, as mentioned above, the hydrolytic saccharification reaction time of the biomass raw material in the reactor is short. In particular, a reaction time necessary for the hydrolytic saccharification of cellulose is very short. The hydrolytic saccharification of cellulose is completed within a short period of time, for example, within one minute.

Accordingly, in the case of adopting the use of the above-described lock hopper, the charging interval of the raw material is longer than the hydrolytic saccharification time. Therefore, in the case of using a complete mixing tank such as the lock hopper, the raw materials that are charged sequentially are mixed together. Consequently, the raw material that has been subjected to the reaction for a long period of time and the raw material that has been subjected to the reaction for a short period of time are discharged at the same time, which causes a reduction in saccharification rate. The same is true in the case of feeding the raw material by the device disclosed in Patent Literature 3.

Solution to Problem

In view of the above, an object of the present invention is to provide a saccharification reaction apparatus capable of: charging a raw material in a suitable condition for hydrolytic saccharification into a reactor by a raw material charging device and hydrolytically saccharifying the raw material efficiently in the reactor.

In order to achieve the above object, the inventors of the present invention conducted experiments aiming to realize efficient hydrolytic saccharification in a reactor. In the experiments, various raw materials in different consolidated states were each charged into a reactor, and subjected to a saccharification reaction in the reactor. Then, the inventors considered that by charging each raw material into the reactor in a predetermined non-consolidated state, the temperature of the raw material could be quickly increased to a saccharification reaction temperature by means of steam.

Based on various experiment results, the inventors came up with a method of charging a raw material in a non-consolidated state into a plug flow reactor by a raw material charging device of a piston pump type. With the method, the inventors have obtained the following findings: by using the method, the temperature of the raw material that has been charged into the reactor can be quickly increased to a suitable temperature for a saccharification reaction in the reactor, and then the raw material can be hydrolytically saccharified efficiently within a short period of time, and in addition, a C6 sugar solution can be recovered, which has conventionally been considered as difficult.

A saccharification reaction apparatus according to the present invention includes: a reactor configured to cause a saccharification reaction of a raw material; and a raw material charging device configured to charge the raw material into the reactor at a predetermined interval. The raw material charging device is configured to charge, into the reactor, the raw material with such a bulk density that the raw material breaks into pieces and is dispersed when charged into the reactor. The reactor includes: a heating steam feeder configured to increase a temperature of the raw material charged from the raw material charging device to a saccharification reaction temperature; and a feeding mechanism configured to discharge the charged raw material through an outlet port after the saccharification reaction of the raw material has been caused under a high temperature and a high pressure for a predetermined time.

According to the above configuration, the raw material charging device charges, into the reactor, the raw material with a suitable bulk density for the saccharification reaction speed of the reactor. Accordingly, the raw material charged into the reactor is dispersed, and thereby the specific surface area of the raw material can be increased, which makes it possible to increase the temperature of the raw material within a short period of time. Therefore, the temperature of the raw material that has been charged into the reactor can be quickly increased to the saccharification reaction temperature, and the raw material can be hydrolytically saccharified efficiently in a predetermined hydrolytic saccharification time. This realizes a saccharification reaction with a high saccharification rate.

The raw material charging device may include: a piston pump configured to charge the raw material into the reactor; a charging pipe configured to guide a piston of the piston pump, the charging pipe including a raw material feeding port; and a gate valve configured to open and close the charging pipe. The piston of the piston pump may include a sealing portion configured to seal between an inner peripheral surface of the charging pipe and the piston. The piston may be configured to isolate between a high-pressure reactor side and a low-pressure raw material feeding port side by the sealing portion in a section from a gate-side end of the raw material feeding port to the gate valve.

According to the above configuration, at the time of charging the raw material into the high-pressure reactor by the piston pump, when the piston reaches the gate-side end of the raw material feeding port of the charging pipe, the sealing portion can seal between the inner peripheral surface of the charging pipe and the piston, and thereby the reactor and the raw material feeding port can be isolated from each other. Accordingly, the gate valve can be opened in a state where the high pressure of the reactor is sealed off by the piston, and thereby the raw material can be stably charged into the high-pressure reactor.

The piston pump may be configured to control either one of a gate-valve-side stop position and a raw-material-feeding-port-side stop position of the piston relative to the gate-side end of the raw material feeding port to render the bulk density of the raw material adjustable.

According to the above configuration, the bulk density of the raw material fed by the piston can be adjusted to a suitable bulk density for the hydrolytic saccharification in the reactor.

The heating steam feeder may be configured to feed heating steam, which is such heating steam that an upper gaseous layer pressure in the reactor becomes higher than a sum of a saturated vapor pressure at a liquid temperature of the raw material fed by the feeding mechanism and a partial pressure of gas other than steam in the reactor.

According to the above configuration, the raw material charged into the reactor with a predetermined non-consolidated bulk density is such that hindrance to the condensation of steam due to the partial pressure of air that is contained in the raw material and that is charged into the reactor together with the raw material is prevented. Therefore, the large specific surface area of the raw material can be rapidly heated up by steam that has a higher pressure than the sum of the saturated vapor pressure at the liquid temperature, which is a hydrolytic saccharification temperature, and the partial pressure of gas other than steam in the reactor. This makes it possible to rapidly increase the temperature of the raw material to a suitable temperature for the hydrolytic saccharification within a short period of time, and hydrolytically saccharify the raw material within a short period of time.

The reactor may include a vent portion, through which air in the raw material charged from the raw material charging device is discharged.

According to the above configuration, air in the raw material that has been charged into the reactor with a predetermined non-consolidated bulk density is discharged from the reactor, and thereby hindrance to the condensation of steam due to the partial pressure of air can be prevented. This also makes it possible to reduce the time for increasing the temperature of the raw material, thereby increasing the saccharification rate.

The saccharification reaction apparatus may include: a mixer configured to mix steam into the raw material to preheat the raw material, and feed the preheated raw material to the raw material charging device; and a flash tank configured to reduce a temperature and a pressure of the raw material discharged from the reactor. The saccharification reaction apparatus may be configured to return steam whose pressure has been reduced in the flash tank to the mixer and mix the steam into the raw material to preheat the raw material, such that the temperature of the preheated raw material becomes lower than or equal to the reaction temperature.

According to the above configuration, steam that is obtained after the temperature and pressure of the raw material discharged from the reactor have been reduced in the flash tank is utilized to preheat the raw material that is to be charged into the reactor. In this manner, energy saving of the apparatus can be realized.

The mixer may be configured to mix an acid catalyst into the raw material.

According to the above configuration, before the raw material is charged into the reactor, the reference acid concentration of the raw material is kept constant, and thereby reduction in saccharification rate due to variation in saccharification rate can be suppressed compared to a case where the acid catalyst is fed in the reactor.

Advantageous Effects of Invention

According to the present invention, the raw material with a suitable bulk density for the saccharification reaction in the reactor can be charged into the reactor by the raw material charging device. Therefore, in the reactor, the temperature of the raw material can be increased to a suitable temperature for the hydrolytic saccharification within a short period of time, and the raw material can be hydrolytically saccharified efficiently.

DESCRIPTION OF EMBODIMENTS

Figure 1:
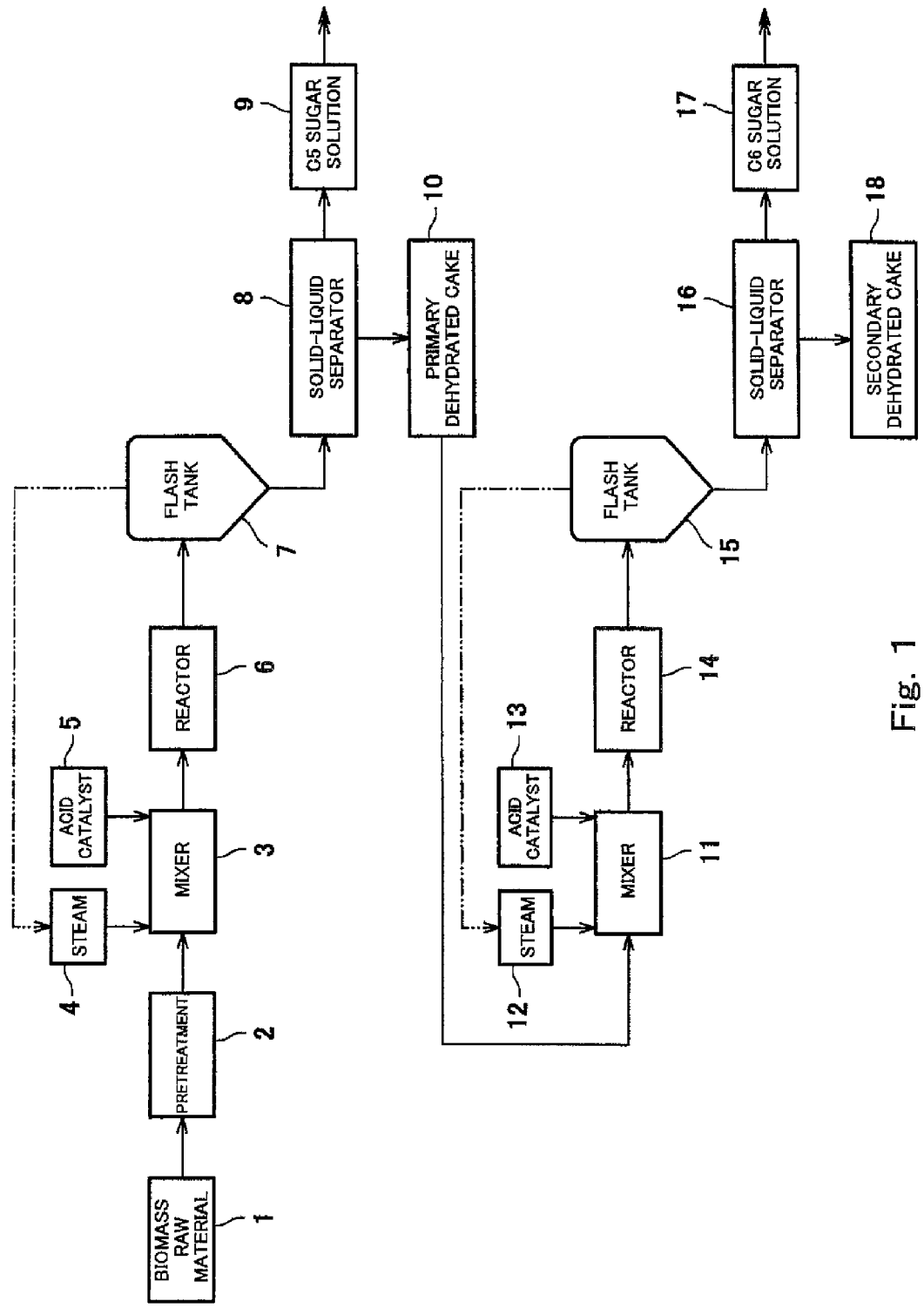
FIG. 1 is a block diagram showing bioethanol production equipment including a saccharification reaction apparatus according to the present invention.

Hereinafter, an embodiment of the present invention is described with reference to the drawings. In the embodiment below, bioethanol production equipment including a saccharification reaction apparatus shown in FIG. 1 is described as one example. The bioethanol production equipment is configured to obtain a C5 sugar solution and a C6 sugar solution through two-staged hydrolytic saccharification.

First, the bioethanol production equipment is briefly described with reference to FIG. 1. A biomass raw material 1 such as bagasse or rice straw is crushed to a predetermined size in pretreatment 2. The raw material is mixed with steam 4 and an acid catalyst 5 in a mixer 3. Then, the raw material is charged into a reactor 6 whose temperature and pressure are set to predetermined temperature and pressure conditions. The raw material is subjected to hydrolytic saccharification for a predetermined period of time in the reactor 6, and is then fed to a flash tank 7, in which the raw material is flash-decompressed. The flash decompressing performed in the flash tank 7 is to rapidly reduce the pressure of the raw material in a slurry state, which is discharged from the reactor 6, thereby vaporizing part of the raw material and reducing the temperature of the raw material. In this manner, the reaction is stopped. A solid and a liquid of the raw material whose temperature and pressure have been reduced in the flash tank 7 are separated as a C5 sugar solution 9 and a primary dehydrated cake 10 by a solid-liquid separator 8.

Then, the primary dehydrated cake 10 is mixed with steam 12 and an acid catalyst 13 in a next mixer 11, thereby becoming a next raw material. The raw material is charged into a reactor 14, whose temperature and pressure are set to next temperature and pressure conditions. In the reactor 14, the raw material is subjected to hydrolytic saccharification for a predetermined period of time, and is then fed to a flash tank 15, in which the raw material is flash-decompressed. A solid and a liquid of the raw material whose temperature and pressure have been reduced in the flash tank 15 are separated as a C6 sugar solution 17 and a secondary dehydrated cake 18 by a solid-liquid separator 16.

The C5 sugar solution 9 and the C6 sugar solution 17 thus obtained are subjected to alcoholic fermentation and then distilled. As a result, bioethanol is produced.

Next, a saccharification reaction apparatus 60 is described in detail with reference to FIG. 2. The saccharification reaction apparatus 60 includes: the mixer 11 and the reactor 14 for obtaining the C6 sugar solution 17 from the primary dehydrated cake 10; and a raw material charging device 20, which is provided between the mixer 11 and the reactor 14. Conditions for obtaining the C6 sugar solution in the reactor 14 are such that, compared to conditions for obtaining the C5 sugar solution in the reactor 6, the reaction temperature and the reaction pressure are higher, and the saccharification reaction time is shorter.

Figure 2:
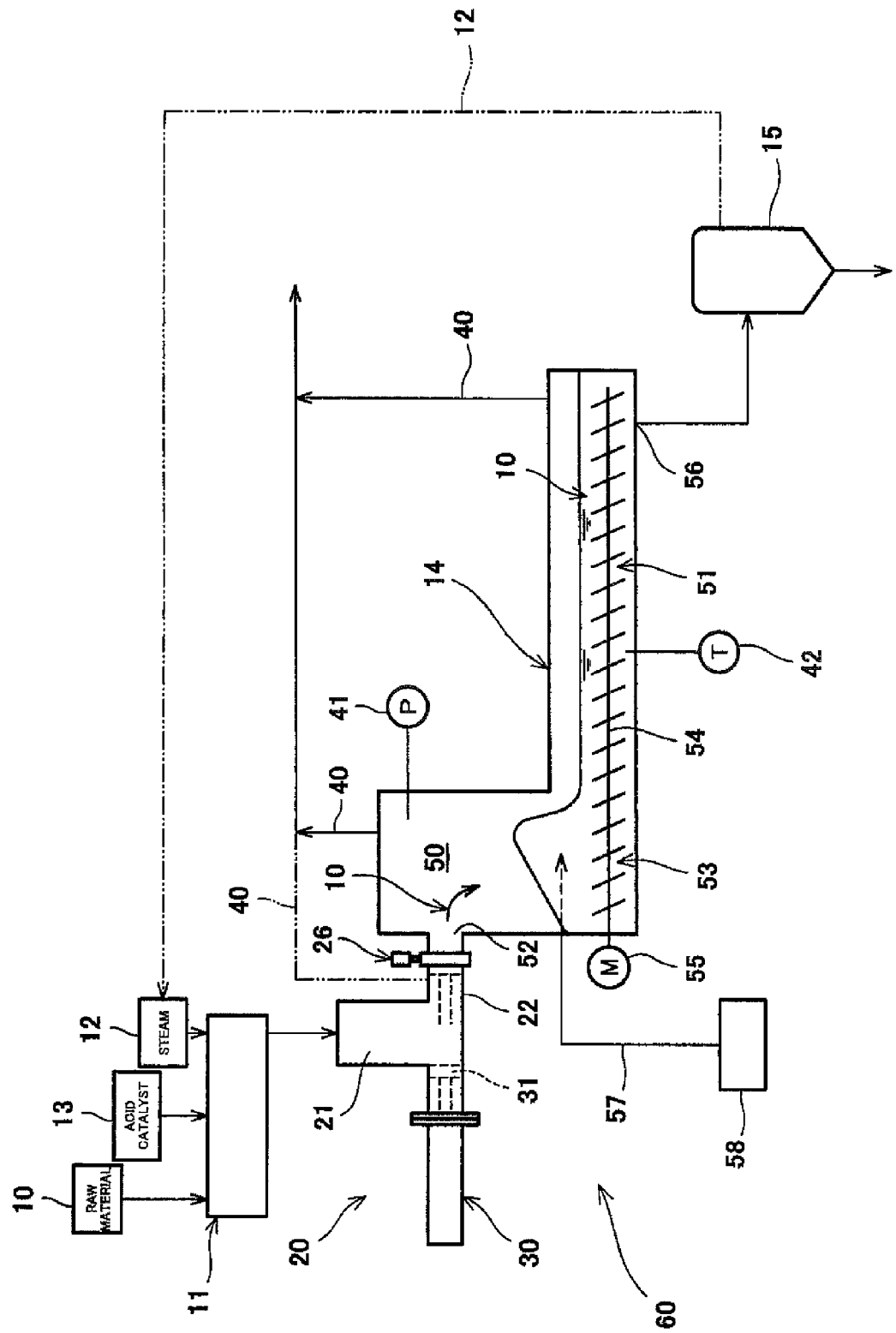
FIG. 2 is a configuration diagram showing the saccharification reaction apparatus according to one embodiment of the present invention.

As shown in FIG. 2, in the mixer 11, the acid catalyst 13 and the steam 12 are mixed into the raw material (in this example, the primary dehydrated cake) 10. In this manner, by mixing the acid catalyst 13 into the raw material 10 before charging the raw material 10 into the reactor 14, the reference acid concentration of the raw material is kept constant, and thereby reduction in saccharification rate due to variation in saccharification rate is suppressed compared to a case where the acid catalyst 13 is fed in the reactor 14.

In the present embodiment, since the raw material 10 is preheated by the steam 12 in the mixer 11, a temperature difference (Δt) that occurs at the time of increasing the temperature of the raw material 10 to a reaction temperature in the reactor 14 described below can be reduced. The preheating using the steam 12 causes the raw material 10 to be preheated to a temperature that is lower than or equal to the reaction temperature in the reactor 14. For example, the raw material 10 is preheated to a temperature of about 120° C. It should be noted that the preheating of the raw material 10 by the steam 12 may be performed as necessary.

The raw material 10 mixed with the acid catalyst 13 and the steam 12 in the mixer 11 is such that, for example, if the moisture in the raw material 10 is less than 50 wt %, it is less likely that the raw material 10 will become slurry in the reactor 14. Therefore, the moisture in the raw material 10 is adjusted to be in the range of about 50 to 80 wt %.

Figure 3:
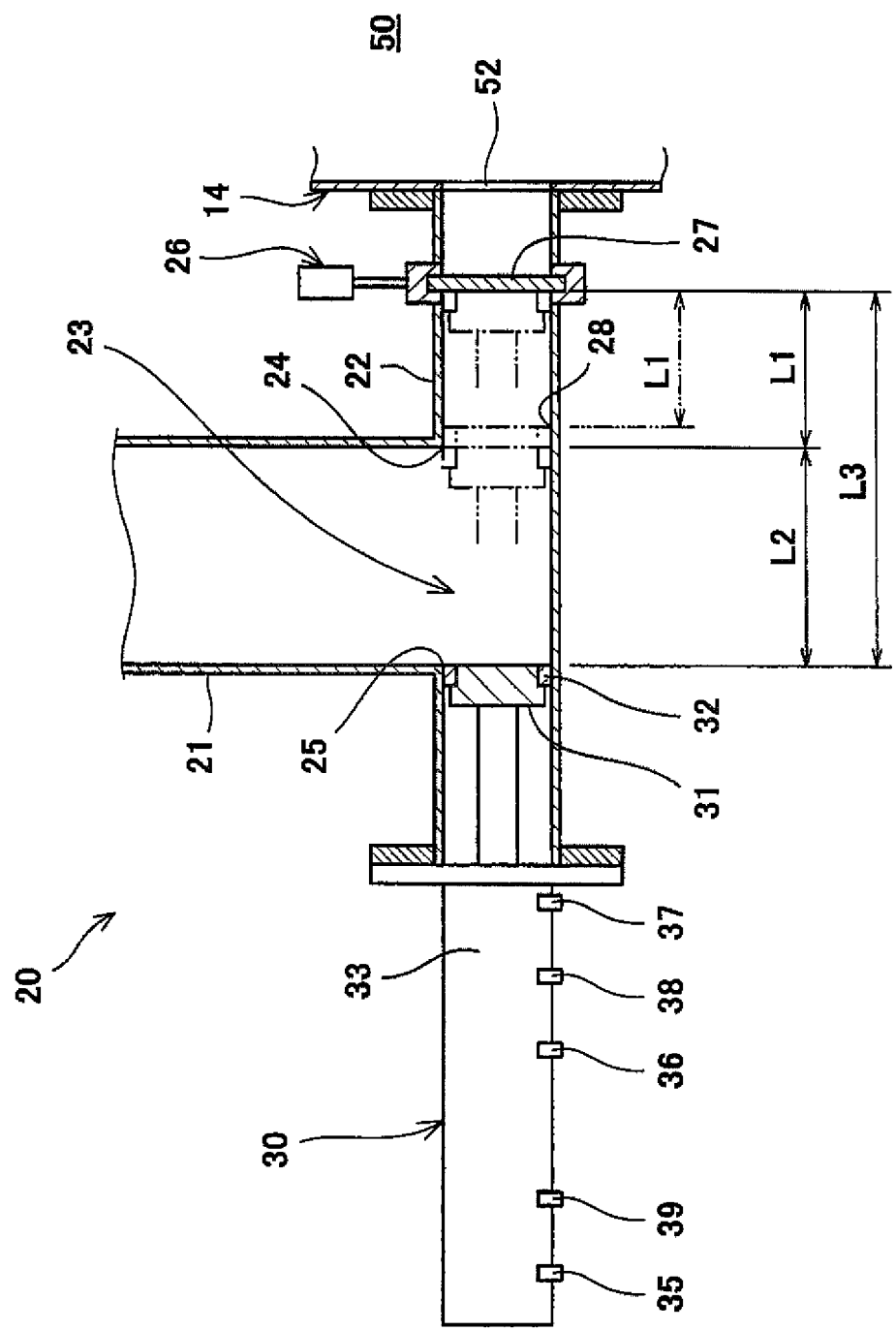
FIG. 3 is a side view of a raw material charging device in the saccharification reaction apparatus shown in FIG. 2.

Then, the raw material 10 is, after being mixed with the acid catalyst 13 in the mixer 11, fed to a hopper 21 of the raw material charging device 20, which is also shown in FIG. 3. The raw material charging device 20 is a device for charging the raw material 10 into the reactor 14. The raw material charging device 20 is configured to charge a fixed amount of raw material 10 from the hopper 21 into the reactor 14 by a piston pump 30 via a charging pipe 22 at predetermined intervals. The piston pump 30 is configured to push the raw material 10 that has been fed to the hopper 21, such that the raw material 10 is pushed out of the hopper 21 toward the reactor 14, thereby charging the raw material 10 into the reactor 14. The charging pipe 22 guides a piston 31 of the piston pump 30.

A gate valve 26 is provided between the piston pump 30 and the reactor 14. Since the reactor 14 is a high-pressure side, when the piston 31 of the piston pump 30 reaches a predetermined position, the gate valve 26 is controlled to isolate (seal) between the piston pump 30 and the reactor 14, and thereafter, the gate valve 26 is controlled to open, such that the raw material 10 is charged into the reactor 14 at predetermined intervals. The predetermined interval is set to be shorter than a time over which the raw material 10 remains in the reactor 14. For example, the raw material 10 is charged into the reactor 14 once in every 20 to 60 seconds. It should be noted that the charging of the raw material will be described below in detail.

As mentioned above, the moisture in the raw material 10 that is to be charged into the reactor 14 by the raw material charging device 20 is adjusted in the mixer 11, such that the moisture is in the range of about 50 to 80 wt %. However, even though the raw material 10 contains moisture in the range of about 50 to 80 wt %, since the raw material 10 is not liquid, the raw material 10 is not easily mixed with steam in the reactor 14.

In view of the above, the raw material 10 with a non-consolidated bulk density is charged into the reactor 14 by the raw material charging device 20. Accordingly, the raw material 10 is dispersed when charged into the reactor 14, so that the temperature of the raw material 10 increases to a saccharification reaction temperature within a short period of time.

That is, by charging the raw material 10 into the reactor 14 with such a bulk density that the raw material 10 is in a non-consolidated flaky state, the charged raw material 10 breaks into pieces and is dispersed in a powdery state. As a result, the raw material 10 has a large surface area coming into contact with heating steam. Specifically, in this manner, the raw material 10 that has been charged and become powdery has a large specific surface area coming into contact with heating steam. The raw material 10 is, owing to the large specific surface area, rapidly heated by the heating steam, and the temperature of the raw material 10 is increased to a suitable temperature for the saccharification reaction within a short period of time. The non-consolidated bulk density of the raw material 10 is set to, for example, about 0.3 to 0.6.

The reactor 14 is configured to obtain a sugar solution by hydrolytically saccharifying a biomass raw material at a high temperature and high pressure. A gaseous layer portion 50 having a predetermined volume is formed in the upper part of the reactor 14, into which the raw material 10 from the piston pump 30 is charged. A liquid layer portion 51 is formed in the lower part of the reactor 14. While the raw material 10 is being fed through the liquid layer portion 51 toward an outlet port 56 over a predetermined reaction time, the raw material 10 is hydrolytically saccharified.

The upper gaseous layer portion 50 is provided with a raw material charging port 52. The distal end of the charging pipe 22 of the piston pump 30 is connected to the raw material charging port 52. The raw material 10 is charged through the raw material charging port 52, and falls onto the top of a transverse feeder 53 provided in the lower liquid layer portion 51. The gaseous layer portion 50 is provided with an upper gaseous layer pressure gauge 41. The liquid layer portion 51 is provided with a liquid thermometer 42.

The transverse feeder 53 provided in the lower part of the reactor 14 is configured such that, when a driving motor 55 drives a biaxial feeding mechanism 54 to rotate, the transverse feeder 53 feeds the raw material 10 transversely while mixing the raw material 10 over a time suitable for the hydrolytic saccharification, and then discharges the hydrolytically saccharified raw material in a slurry state through the outlet port 56. The reactor 14 is a plug flow reactor configured to sequentially feed the raw materials 10 that have been charged from the raw material charging port 52 toward the outlet port 56. The raw material 10 reacts and becomes high-concentration slurry while the raw material 10 is being fed by the transverse feeder 53 under the high-temperature and high-pressure environment in the reactor 14.

In the present embodiment, the feeding mechanism 54 of the transverse feeder 53 is configured as a biaxial feeding mechanism. However, the feeding mechanism 54 is not limited to a particular type of feeding mechanism, so long as the feeding mechanism 54 is configured to convey the raw material 10 to the outlet port 56 over the predetermined reaction time.

At the raw material charging port 52 side of the reactor 14, heating steam 57 is fed to the raw material 10 that has been charged through and fallen from the raw material charging port 52. The heating steam 57 is fed from a heating steam feeder 58. The heating steam 57 is such high-temperature steam that the upper gaseous layer pressure in the reactor 14 becomes higher than the sum of the saturated vapor pressure at the temperature of the liquid layer portion and the partial pressure of gas other than steam. By means of the heating steam 57, the temperature of the raw material 10 that has been charged through the raw material charging port 52 is quickly increased. For example, if the temperature of the liquid layer portion in the reactor 14 is in the range of 240 to 280° C., the heating steam 57 to be fed is high-temperature steam with a temperature of about 250 to 300° C. By feeding the high-temperature heating steam 57, the temperature of the raw material 10 is increased to the saccharification reaction temperature within a short period of time. For example, the temperature of the raw material 10 can be increased to the saccharification reaction temperature within ten seconds, during which the temperature of the raw material 10 can be increased from a temperature of about 20 to 120° C. to a temperature of about 240 to 280° C.

The heating steam feeder 58 feeds the heating steam 57, which is such high-pressure steam that the following inequation holds true: saturated vapor pressure of the liquid layer portion 51+partial pressure of air<internal upper gaseous layer pressure. In this example, the heating steam feeder 58 feeds steam whose temperature is in the range of 250 to 300° C. As mentioned above, the pressure of the gaseous layer in the upper space in the reactor 14 is adjusted to be higher than the sum of the saturated vapor pressure of the liquid layer portion 51 and the partial pressure of gas other than steam. As a result, hindrance to the condensation of steam due to the partial pressure of air is prevented. Also in this manner, the time for increasing the temperature of the raw material 10 is reduced, and thereby the saccharification rate is improved.

In the present embodiment, air is released through vent pipes 40 from above the raw material charging port 52 and from above an end edge of the transverse feeder 53. When the raw material 10 with a non-consolidated bulk density is charged into the reactor 14 by the piston pump 30 as described above, air is contained in the raw material 10. The air is discharged through the vent pipes 40, and thereby the following problem is prevented: the partial pressure of steam in the reactor 14 decreases, due to which the steam is not easily condensed, and as a result, the temperature increase of the raw material 10 becomes slower. The release of air through vent pipes 40 may include release of air through a vent pipe 40 that connects to the charging pipe 22 of the raw material charging device 20. As described above, by releasing the air so that an excessive amount of air will not remain in the reactor 14, the partial pressure of air in the reactor 14 is reduced, and thereby the condensation of steam is accelerated. Also in this manner, the time for increasing the temperature of the raw material 10 is reduced, and thereby the saccharification rate is improved.

An end portion of the transverse feeder 53 in its feeding direction is provided with the outlet port 56, through which the hydrolytically saccharified raw material 10 is discharged. The raw material 10 discharged through the outlet port 56 is fed to the flash tank 15, in which the raw material 10 is flash-decompressed, and then the raw material 10 is fed to the solid-liquid separator (FIG. 1) 16.

Further, in the present embodiment, steam that is generated in the upper part of the flash tank 15 when the flash decompressing is performed in the flash tank 15 is led to the mixer 11 and utilized as the steam 12 for preheating the raw material. By feeding the steam 12 from the flash tank 15 to the mixer 11 to utilize the steam 12 for preheating the raw material, the energy saving of the entire apparatus is realized.

Next, the raw material charging device 20 is described in detail with reference to FIG. 3. The raw material charging device 20 includes: the gate valve 26 provided at a position that is slightly away from the raw material charging port 52 of the reactor 14; the hopper 21 provided at a position that is away from the gate valve 26 by a predetermined distance; and the piston pump 30 configured to push the raw material 10 that has been fed to the hopper 21, such that the raw material 10 is pushed out of the hopper 21.

A controller controls the gate valve 26 to open or close the charging pipe 22. A gate member 27 opens or closes the charging pipe 22.

A distance L1 between a hopper-side end face of the gate member 27 and a gate-side end (a raw material feeding port end) 24 of a raw material feeding port 23 provided at the bottom of the hopper 21 is slightly less than a raw material feeding port distance L2 at the bottom of the hopper 21.

The distal end portion of the piston 31 of the piston pump 30 is provided with a sealing portion 32. The sealing portion 32 exerts a sealing function of sealing between the piston 31 and the inner peripheral surface of the charging pipe 22 in a section from the gate-side end 24 of the raw material feeding port 23 to the gate valve 26. Accordingly, the piston 31 of the piston pump 30 pushes the raw material 10 that has been fed to the raw material feeding port 23 from a piston-pump-side end 25 of the raw material feeding port 23 toward the gate valve. When the piston 31 is inserted into the charging pipe 22 from the gate-side end 24 of the raw material feeding port 23, the sealing portion 32 seals between the piston 31 and the charging pipe 22. It should be noted that, in the description below, the reference position for the distance L1 at the raw material feeding port side corresponds to the gate-side end 24. However, alternatively, as indicated by two-dot chain lines, the reference position for the distance L1 at the raw material feeding port side may be a position 28, which is slightly away from the gate-side end 24 toward the gate valve so that the gate member 27 will be opened in a state where the charging pipe 22 is fully sealed by the sealing portion 32 of the piston 31.

Therefore, in a state where the sealing portion 32 of the piston 31 seals between the piston 31 and the charging pipe 22, even if the gate valve 26 is opened, pressure will not be relieved from the high-pressure reactor 14 side toward the low-pressure raw material feeding port 23.

When the charging pipe 22 is in a state of being sealed by the piston 31, the gate member 27 is opened and the piston 31 of the piston pump 30 is expanded to the position of the gate valve 26. As a result, the raw material 10 in the charging pipe 22 is charged into the reactor 14.

Thereafter, the piston 31 is retracted, and the gate member 27 is closed before the piston 31 reaches the gate-side end 24 of the raw material feeding port 23. In this manner, the gate valve 26 is closed in a state where the charging pipe 22 is sealed by the sealing portion 32 of the piston 31. Therefore, pressure will not be relieved from the high-pressure reactor 14 side toward the low-pressure raw material feeding port 23.

In the present embodiment, stroke distances over which the piston 31 of the piston pump 30 is expanded and contracted are controlled by sensors. In this example, a cylinder 33 configured to expand and contract the piston 31 is provided with position sensors 35 to 39. These position sensors 35 to 39 detect the position of the piston 31. In accordance with the detected position of the piston 31, opening and closing of the gate member 27 of the gate valve 26 are controlled in the above-described manner.

Figure 4A:
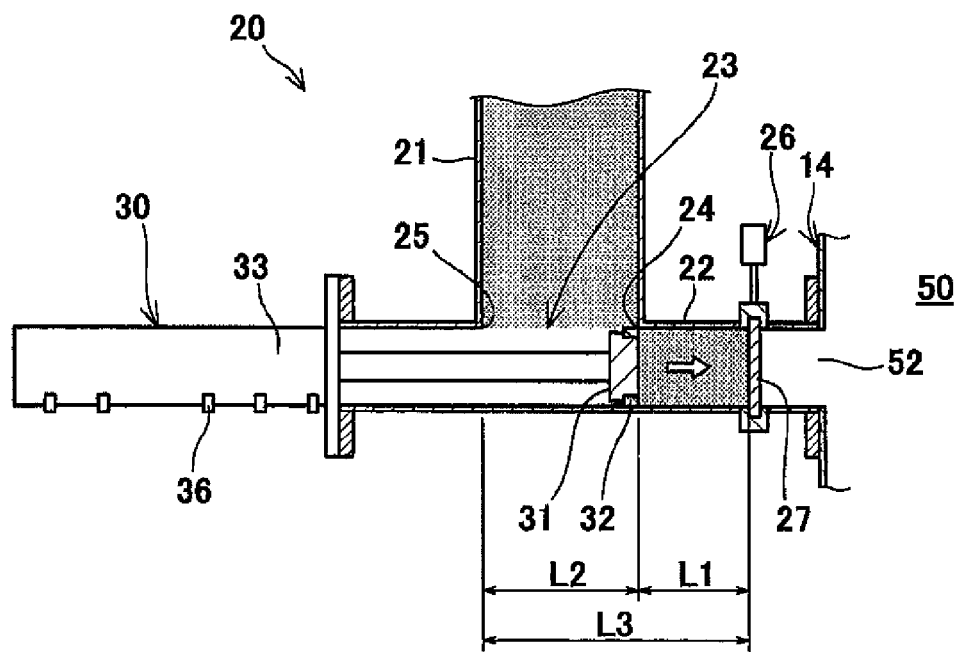
FIG. 4A is a side view showing operating position control of the raw material charging device shown in FIG. 3.
Figure 4B:
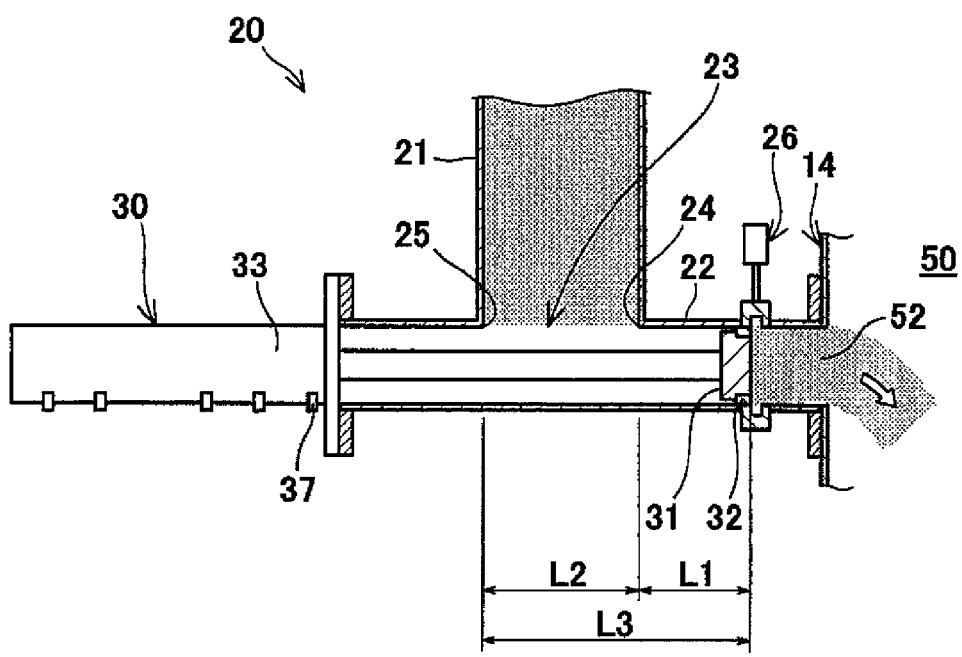
FIG. 4B is a side view showing next operating position control of the raw material charging device shown in FIG. 4A.
Figure 4C:
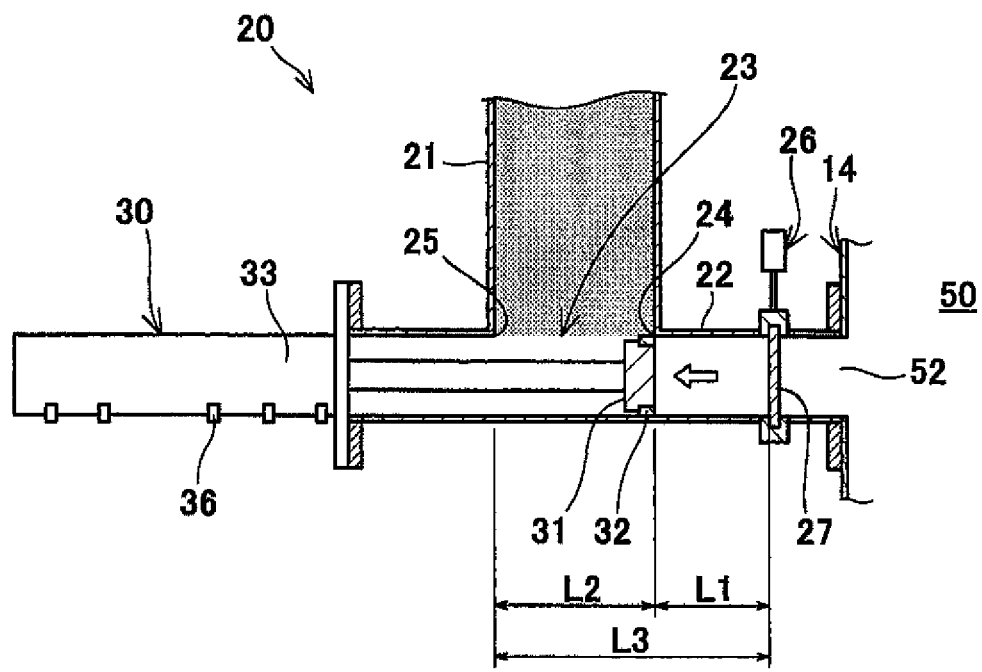
FIG. 4C is a side view showing next operating position control of the raw material charging device shown in FIG. 4B.
Figure 5A:
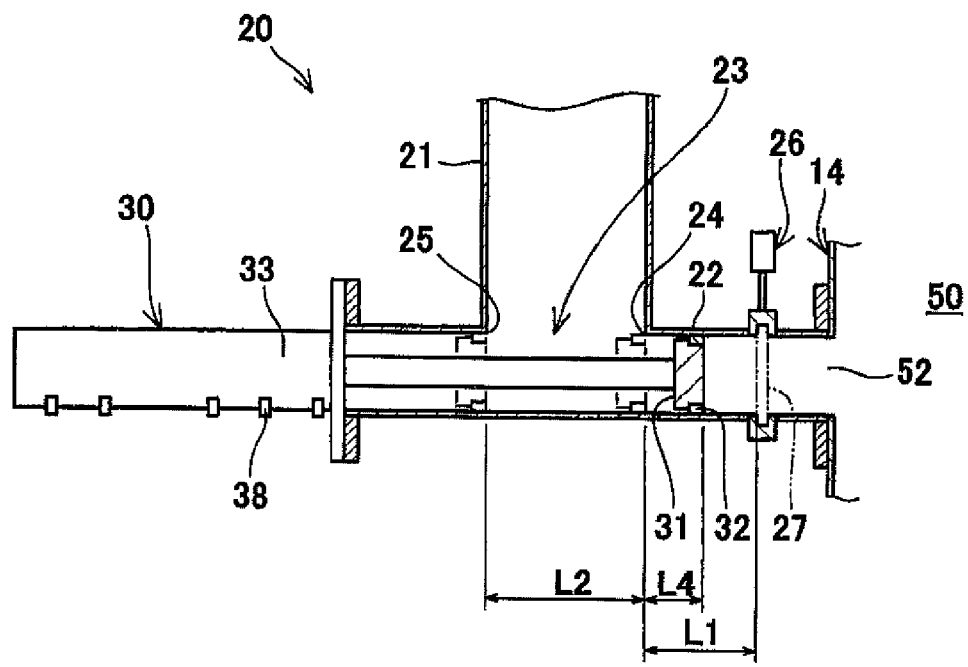
FIG. 5A is a side view showing an example of operating position control, which is different from the operating position controls of the raw material charging device shown in FIGS. 4A to 4C.
Figure 5B:
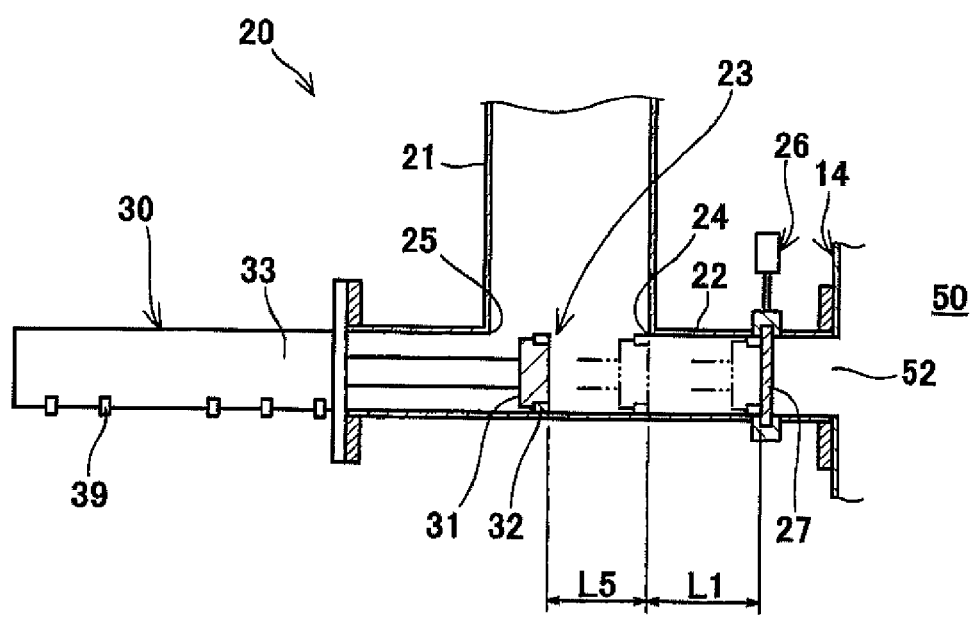
FIG. 5B is side view showing an example of operating position control, which is different from the operating position controls of the raw material charging device shown in FIGS. 4A to 4C and 5A.

In the present embodiment, as shown in FIG. 4A to FIG. 4C referred to below, the cylinder 33 is provided with: the position sensor 35 configured to detect that the piston 31 of the piston pump 30 is positioned at the piston-pump-side end 25 of the raw material feeding port 23; the position sensor 36 configured to detect that the piston 31 is positioned at the gate-side end 24 of the raw material feeding port 23; and the position sensor 37 configured to detect that the piston 31 is positioned on the hopper-side end face of the gate member 27. As shown in FIG. 5A and FIG. 5B referred to below, the cylinder 33 is also provided with: the position sensor 38 configured to detect that the piston 31 has reached a position corresponding to a distance L4; and the position sensor 39 configured to detect that the piston 31 has reached a position corresponding to a distance L5. Limit switches or other configurations may be utilized to realize these position sensors 35 to 39.

Next, operating position control is described with reference to FIG. 4A to FIG. 4C in relation to the distance L1 from the gate member 27 of the charging pipe 22 to the gate-side end 24 of the raw material feeding port 23, the raw material feeding port distance L2 of the hopper 21, and a stroke L3 of the piston pump 30 for the piston 31 to be positioned on the hopper-side end face of the gate member 27.

FIG. 4A shows a state where the piston 31 of the piston pump 30 is expanded from the state shown in FIG. 3. By expanding the piston 31, the raw material 10 at the bottom of the hopper 21 in an amount corresponding to the raw material feeding port distance L2 is pushed toward the gate valve 26. Then, when the piston 31 reaches the gate-side end 24 of the raw material feeding port 23, the sealing portion 32 around the piston 31 comes into contact with the charging pipe 22, thereby sealing between the piston 31 and the inner peripheral surface of the charging pipe 22. As a result, the raw material 10 in the amount corresponding to the raw material feeding port distance L2 is moved to a portion of the charging pipe 22, the portion corresponding to the distance L1 between the gate member 27 of the gate valve 26 and the gate-side end 24 of the raw material feeding port 23, such that the raw material 10 is in a slightly pushed state. Also, in this manner, the high-pressure reactor 14 side and the low-pressure raw material feeding port 23 side can be isolated from each other.

Next, as shown in FIG. 4B, the gate member 27 is opened, and the piston 31 is expanded by a stroke L1. In this manner, the raw material 10 is charged into the reactor 14. In this example, the raw material 10 is slightly pushed in the charging pipe 22 such that the raw material 10 has a predetermined bulk density (e.g., about 0.3 to 0.6), and then the raw material 10 is charged into the reactor 14. Therefore, when the raw material 10 is charged into the reactor 14, the raw material 10 breaks into pieces and is dispersed in a powdery state. By dispersing the raw material 10 at the time of charging, the specific surface area of the raw material 10 increases, and consequently, the raw material 10 is quickly heated to the saccharification reaction temperature by means of the heating steam.

In the present embodiment, as described above, the raw material 10 is preheated to such a temperature as not to cause the saccharification reaction to progress (e.g., to a temperature in the range of 100 to 120° C.). In this manner, the temperature increase that is to be caused by heating after the raw material 10 is charged into the reactor 14 is made small, and thereby the temperature of the raw material 10 is rapidly increased to the reaction temperature. By adopting this configuration, the steam in the flash tank 15 is effectively utilized as described above, and the degree of temperature increase caused in the reactor 14 is made small. In this manner, energy saving is realized.

Next, as shown in FIG. 4C, the gate member 27 is closed while the piston 31 is being contracted by the distance L1 to the gate-side end 24 of the raw material feeding port 23. Thereafter, the piston 31 is contracted to the piston-pump-side end 25 of the raw material feeding port 23 to be in the initial state shown in FIG. 3.

The raw material 10 is charged in this manner by the piston pump 30, for example, once in every 20 to 60 seconds, i.e., at charging intervals of 20 to 60 seconds. The time over which the raw material 10 remains in the reactor 14 (i.e., the conveyance time) is very short, for example, several tens of seconds to one minute. However, the charging of the raw material 10 is performed at the intervals, each of which is shorter than the conveyance time. Thus, the raw material 10 is charged into the reactor 14 in short cycles in such a manner that, as described above, the raw material 10 has a non-consolidated bulk density and is in a flaky state at the time of being charged into the reactor 14. Accordingly, the raw materials 10 are sequentially fed through the reactor 14, and each raw material 10 is hydrolytically saccharified efficiently in a predetermined short hydrolytic saccharification time. In this manner, increase in the saccharification rate is realized.

Next, examples of different operating position control by means of the piston pump 30 and the gate valve 26 are described with reference to FIG. 5A and FIG. 5B. It should be noted that positions corresponding to distances L4 and L5 in FIGS. 5A and 5B are shown in an exaggerated manner for the sake of convenience of the description.

The example shown in FIG. 5A is an example of settings that are applied when the bulk density of the raw material 10 is desired to be slightly higher (i.e., the raw material 10 is desired to be slightly more consolidated) than in the example shown in FIG. 4A to FIG. 4C. In this example, the expanded position of the piston 31 at the time of charging the raw material (i.e., at the time of opening the gate member 27) is limited to the position corresponding to the distance L4, such that the piston 31 does not reach the hopper-side end face of the gate member 27. The distance L4 is detected by the position sensor 38 provided on the cylinder 33.

By limiting the expansion length of the piston 31 as described above, the raw material 10 that is to be charged from the charging pipe 22 into the reactor 14 slightly remains in front of the gate member 27. Accordingly, next, when the raw material 10 in an amount corresponding to the raw material feeding port distance L2 is moved by the piston 31 toward the charging pipe 22 and then the piston 31 has reached the gate-side end 24, the new raw material 10 is pushed against the raw material 10 remaining in front of the gate member 27. In this manner, in the charging pipe 22, the raw material 10 can be consolidated to a slightly higher degree.

Then, by opening the gate member 27 and expanding the piston 31 by the distance L4, the raw material 10 with the higher bulk density can be charged into the reactor 14. This example of operating position control is applied to a case where the raw material needs to be slightly consolidated before being charged into the reactor 14.

At the time of expanding the piston 31 to charge the raw material 10, the gate member 27 may be in a closed state as indicated by two-dot chain lines, and the piston 31 may be pushed in from the gate-side end 24 to the position corresponding to the distance L4. Then, when the piston 31 has reached the position corresponding to the distance L4, the gate member 27 may be opened and the piston 31 may be further expanded to the position corresponding to the distance L1 to charge the raw material 10 into the reactor 14. In this manner, the raw material 10 in an amount corresponding to the raw material feeding port distance L2 can be consolidated in the charging pipe 22 in front of the gate member 27 by the distance L4 to increase the bulk density, and the raw material 10 with the increased bulk density can be charged into the reactor 14. This example of operating position control is also applied to a case where the raw material needs to be slightly consolidated before being charged into the reactor 14.

The example shown in FIG. 5B is an example of settings that are applied when the bulk density of the raw material 10 is desired to be slightly lower (i.e., the raw material 10 is desired to be more flaky), or the feeding amount of the raw material 10 is desired to be less, than in the example shown in FIG. 4A to FIG. 4C. In this example, the contracted position of the piston 31 is limited to the position corresponding to the distance L5 such that, at the bottom of the hopper 21, the piston 31 is stopped in the middle of being contracted by the raw material feeding port distance L2. The distance L5 is detected by the position sensor 39 provided on the cylinder 33.

By limiting the contraction length of the piston 31 as described above, the raw material 10 in an amount corresponding to the distance L5 out of the raw material feeding port distance L2 at the bottom of the hopper 21 is pushed in between the gate-side end 24 of the charging pipe 22 and the gate member 27 before the piston 31 seals the gate-side end 24. Thus, the amount of raw material 10 to be pushed in between the gate-side end 24 of the charging pipe 22 and the gate member 27 is reduced. In this manner, the amount of raw material 10 moved to the charging pipe 22 is reduced, and thereby the raw material 10 is prevented from being consolidated. Also, the feeding amount of the raw material 10 can be reduced.

Then, by opening the gate member 27 and expanding the piston 31 by the distance L1, the raw material 10 with the lower bulk density can be charged into the reactor 14. This example of operating position control is applied to, for example, the case of charging the raw material 10 that has previously been slightly consolidated into the reactor 14 without further consolidating the raw material 10.

When settings of the distance L1 and the raw material feeding port distance L2 are made, the bulk density adjustment of the raw material 10 as described above can be performed by adjusting the expanded and contracted positions of the piston 31 with reference to the position of the gate-side end 24 of the charging pipe 22. The adjustment of the expanded and contracted positions of the piston 31 can be performed by adjusting the positions of the position sensors 38 and 39.

As described above, according to the saccharification reaction apparatus 60, the raw material 10 can be charged into the reactor 14 highly frequently by the piston pump 30 of the raw material charging device 20 in a case where the raw material 10 is desired to be charged into the reactor 14 at short intervals in, for example, bioethanol production. In addition, the raw material 10 with such a bulk density that the temperature of the raw material 10 can be increased to a suitable temperature for the reaction in the reactor 14 within a short period of time can be charged into the reactor 14.

Moreover, even if the moisture condition and the like vary depending on the raw material 10, adjustments of, for example, the consolidated state of the raw material 10 to be charged into the reactor 14 can be made by controlling the piston pump 30 of the raw material charging device 20. Therefore, the raw material 10 whose bulk density has been adjusted to a suitable bulk density for the reactor 14 can be charged into the reactor 14. This realizes a stable reaction with a high saccharification rate in the reactor 14.

By charging the raw material 10 into the reactor 14 by means of the piston pump 30, the raw material 10 can be charged into the reactor 14 while leaving no raw material 10 inside the charging pipe 22.

The above description of the embodiment describes, as one example, the bioethanol production equipment, which obtains a C5 sugar solution and a C6 sugar solution through two-staged hydrolytic saccharification of the biomass raw material 10. However, the present embodiment is applicable also to other equipment if the other equipment is intended to charge a similar type of raw material into a reactor and cause a reaction of the raw material in the reactor within a short period of time. That is, the above description of the embodiment merely gives a non-limiting example.

The above description of the embodiment describes two examples (FIG. 5A, FIG. 5B) as examples of movement control of the piston 31 of the piston pump 30. These movement controls may be combined together, and also, different operating position control may be performed in accordance with different conditions. Thus, the operating position control of the piston pump 30 is not limited to the above-described embodiment. In addition, the operating position control of the piston 31 can be performed not only by utilizing limit switches but also by utilizing hydraulic pressure driving the piston 31, such that the bulk density of the raw material 10 becomes a suitable bulk density. That is, the above description of the embodiment merely gives non-limiting examples.

Moreover, in the above embodiment, devices such as a drain valve, a depressurizing valve, and a pressure equalizing valve may be provided on the raw material feeding port side near the gate valve 26 of the charging pipe 22.

The above description of the embodiment describes non-limiting examples, and various modifications can be made to the embodiment without departing from the spirit of the present invention. Thus, the present invention is not limited to the above-described embodiment.

INDUSTRIAL APPLICABILITY

The saccharification reaction apparatus according to the present invention is applicable particularly to a case where it is desired to hydrolytically saccharify a biomass raw material efficiently and increase the saccharification rate.

REFERENCE SIGNS LIST 10 raw material (primary dehydrated cake)
11 mixer
12 steam
13 acid catalyst
14 reactor
15 flash tank
16 solid-liquid separator
17 C6 sugar solution
18 secondary dehydrated cake
20 raw material charging device
21 hopper
22 charging pipe
23 raw material feeding port
24 gate-side end
25 piston-pump-side end
26 gate valve
27 gate member
30 piston pump
31 piston
32 sealing portion 33 cylinder
35 to 39 position sensor
40 vent pipe
41 upper gaseous layer pressure gauge
42 liquid thermometer
50 gaseous layer portion
51 liquid layer portion
52 raw material charging port
53 transverse feeder
54 feeding mechanism
55 driving motor
56 outlet port
57 heating steam
58 heating steam feeder
60 saccharification reaction apparatus
L1 distance
L2 raw material feeding port distance
L3 stroke
L4, L5 distance

The invention claimed is:

1. A saccharification reaction apparatus comprising:
a reactor configured to cause a saccharification reaction of a biomass raw material; and
a raw material charging device configured to charge the biomass raw material into the reactor at a predetermined interval and with such a bulk density that the biomass raw material is dispersed when charged into the reactor, the raw material charging device including:
  a piston pump configured to charge the biomass raw material into the reactor;
  a charging pipe configured to guide a piston of the piston pump, the charging pipe including a raw material feeding port; and
  a gate valve configured to open and close the charging pipe;
the reactor includes:
  a heating steam feeder configured to feed heating steam into the reactor to increase a temperature of the biomass raw material charged from the raw material charging device to a saccharification reaction temperature of 240° C. to 280° C.; and
  a feeding mechanism configured to discharge the charged biomass raw material through an outlet port after the saccharification reaction of the biomass raw material has been performed for a predetermined time while the heating steam is being fed into the reactor.

2. The saccharification reaction apparatus according to claim 1, wherein:
the piston of the piston pump includes a sealing portion configured to seal between the charging pipe and the piston, and
the piston is configured such that a section from a gate-side end of the raw material feeding port to the gate valve is divided by the sealing portion into a high-pressure reactor side and a low-pressure raw material feeding port side.

3. The saccharification reaction apparatus according to claim 2, wherein the piston pump is configured to control either one of a gate-valve-side stop position and a raw-material-feeding-port-side stop position of the piston relative to the gate-side end of the raw material feeding port to render the bulk density of the biomass raw material adjustable.

4. The saccharification reaction apparatus according to claim 1, wherein the heating steam feeder is configured to feed the heating steam, such that an upper gaseous layer pressure in the reactor becomes higher than a sum of a saturated vapor pressure at a liquid temperature of the biomass raw material fed by the feeding mechanism and a partial pressure of gas other than steam.

5. The saccharification reaction apparatus according to claim 1, wherein the reactor includes a vent portion, through which air in the raw material charged from the biomass raw material charging device is discharged.

6. The saccharification reaction apparatus according to claim 1, further comprising:
a mixer configured to mix steam into the biomass raw material to preheat the biomass raw material, and feed the preheated biomass raw material to the raw material charging device; and
a flash tank configured to reduce a temperature and a pressure of the biomass raw material discharged from the reactor, wherein
the saccharification reaction apparatus is configured to return steam that has a pressure that has been reduced in the flash tank to the mixer, and to mix the steam into the biomass raw material to preheat the biomass raw material, such that the temperature of the preheated biomass raw material becomes lower than or equal to the saccharification reaction temperature.

7. The saccharification reaction apparatus according to claim 6, wherein the mixer is configured to mix an acid catalyst into the biomass raw material.

* * * * *